United States Patent
Vitello et al.

(10) Patent No.: US 9,855,191 B1
(45) Date of Patent: Jan. 2, 2018

(54) TAMPER EVIDENT SHIELD ASSEMBLY WITH TRACKING

(71) Applicants: Jonathan J. Vitello, Fort Lauderdale, FL (US); Brandon Hunt, Miami, FL (US)

(72) Inventors: Jonathan J. Vitello, Fort Lauderdale, FL (US); Brandon Hunt, Miami, FL (US)

( * ) Notice: Subject to any disclaimer, the term of this patent is extended or adjusted under 35 U.S.C. 154(b) by 393 days.

(21) Appl. No.: 14/520,198

(22) Filed: Oct. 21, 2014

Related U.S. Application Data

(60) Provisional application No. 61/984,347, filed on Apr. 25, 2014, provisional application No. 61/913,571, filed on Dec. 9, 2013.

(51) Int. Cl.
*A61J 1/14* (2006.01)
*A61J 1/18* (2006.01)
*A61M 5/50* (2006.01)

(52) U.S. Cl.
CPC . *A61J 1/14* (2013.01); *A61J 1/18* (2013.01); *A61J 2200/70* (2013.01); *A61M 5/5086* (2013.01)

(58) Field of Classification Search
CPC ............. A61J 1/14; A61J 1/18; A61M 5/5086
See application file for complete search history.

(56) References Cited

U.S. PATENT DOCUMENTS

| | | |
|---|---|---|
| 1,970,631 A | 8/1934 | Sherman |
| 2,834,346 A | 5/1958 | Adams |
| 2,888,015 A | 5/1959 | Hunt |
| 3,245,567 A | 4/1966 | Knight |
| 3,364,890 A | 1/1968 | Andersen |
| 3,706,307 A | 12/1972 | Hasson |
| 3,747,751 A | 7/1973 | Miller et al. |
| 3,905,375 A | 9/1975 | Toyama |
| 4,216,585 A | 8/1980 | Hatter |
| 4,216,872 A | 8/1980 | Bean |
| 4,313,539 A | 2/1982 | Raines |
| 4,420,085 A | 12/1983 | Wilson et al. |
| 4,430,077 A | 2/1984 | Mittleman et al. |
| 4,457,445 A * | 7/1984 | Hanks .................... B65D 55/06 220/214 |
| 4,521,237 A | 6/1985 | Logothetis |
| 4,530,697 A | 7/1985 | Kuhlemann et al. |
| 4,571,242 A | 2/1986 | Klein et al. |

(Continued)

Primary Examiner — Bradley Osinski
(74) Attorney, Agent, or Firm — Malloy & Malloy, P.L.

(57) ABSTRACT

A shield assembly for enclosing and restricting access to the port of a container including a tamper evident structure. A housing includes two segments movable between closed and opened orientations. A hollow interior of the housing, when in the closed orientation, substantially corresponds to the enclosed port. A lock assembly includes male and female members wherein a frangible structure interconnects the female member in engaging relation to the male member in a locked orientation. Passage of the male member through the female member from the locked position into an unlocked position results in detachment of the frangible structure and an enlargement of the female member sufficient to restrict the lock assembly from assuming the locked position. A tracking assembly is included and operative to identify and distinguish a plurality of shield assemblies and/or their components from one another.

27 Claims, 7 Drawing Sheets

(56) References Cited

U.S. PATENT DOCUMENTS

| | | |
|---|---|---|
| 4,589,171 A | 5/1986 | McGill |
| 4,667,837 A | 5/1987 | Vitello et al. |
| 4,693,707 A | 9/1987 | Dye |
| 4,726,483 A | 2/1988 | Drozd |
| 4,743,231 A | 5/1988 | Kay et al. |
| 4,760,847 A | 8/1988 | Vaillancourt |
| 4,832,695 A | 5/1989 | Rosenberg et al. |
| 4,834,706 A | 5/1989 | Beck et al. |
| 4,844,906 A | 7/1989 | Hermelin et al. |
| 4,919,285 A | 4/1990 | Roof et al. |
| 5,009,323 A | 4/1991 | Montgomery et al. |
| 5,049,129 A | 9/1991 | Zdeb et al. |
| 5,135,496 A | 8/1992 | Vetter et al. |
| 5,165,560 A | 11/1992 | Enniss, III et al. |
| 5,230,429 A | 7/1993 | Etheredge, III |
| 5,292,308 A | 3/1994 | Ryan |
| 5,328,466 A | 7/1994 | Denmark |
| 5,328,474 A | 7/1994 | Raines |
| 5,356,380 A | 10/1994 | Hoekwater et al. |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,624,402 A | 4/1997 | Imbert |
| 5,702,374 A | 12/1997 | Johnson |
| 5,776,124 A | 7/1998 | Wald |
| 5,785,691 A | 7/1998 | Vetter et al. |
| 5,807,343 A | 9/1998 | Tucker et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,989,227 A | 11/1999 | Vetter et al. |
| 6,000,548 A | 12/1999 | Tsals |
| 6,021,824 A | 2/2000 | Larsen et al. |
| 6,027,482 A | 2/2000 | Imbert |
| 6,068,614 A | 5/2000 | Kimber et al. |
| 6,126,640 A | 10/2000 | Tucker et al. |
| 6,190,364 B1 | 2/2001 | Imbert |
| 6,193,688 B1 | 2/2001 | Balestracci et al. |
| 6,196,998 B1 | 3/2001 | Jansen et al. |
| 6,280,418 B1 | 8/2001 | Reinhard et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,726,652 B2 | 4/2004 | Eakins et al. |
| 6,726,672 B1 | 4/2004 | Hanly et al. |
| 6,764,469 B2 | 7/2004 | Broselow |
| 6,821,268 B2 | 11/2004 | Balestracci |
| 6,921,383 B2 | 7/2005 | Vitello |
| 6,942,643 B2 | 9/2005 | Eakins et al. |
| 7,141,286 B1 | 11/2006 | Kessler et al. |
| 7,182,256 B2 | 2/2007 | Andreasson et al. |
| 7,374,555 B2 | 5/2008 | Heinz et al. |
| 7,404,500 B2 | 7/2008 | Marteau et al. |
| 7,425,208 B1 | 9/2008 | Vitello |
| 7,437,972 B2 | 10/2008 | Yeager |
| 7,588,563 B2 | 9/2009 | Guala |
| 7,632,244 B2 | 12/2009 | Buehler et al. |
| 7,641,636 B2 | 1/2010 | Moesli et al. |
| 7,735,664 B1 | 6/2010 | Peters et al. |
| 7,762,988 B1 | 7/2010 | Vitello |
| 7,802,313 B2 | 9/2010 | Czajka |
| 7,918,830 B2 | 4/2011 | Langan et al. |
| 8,079,518 B2 | 12/2011 | Turner et al. |
| 8,091,727 B2 | 1/2012 | Domkowski |
| 8,140,349 B2 | 3/2012 | Hanson et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| 8,556,074 B2 * | 10/2013 | Turner .................. A61F 2/0095 206/339 |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| 8,702,674 B2 | 4/2014 | Bochenko |
| 8,864,021 B1 | 10/2014 | Vitello |
| 8,864,707 B1 | 10/2014 | Vitello |
| 8,864,708 B1 | 10/2014 | Vitello |
| 8,945,082 B2 | 2/2015 | Geiger et al. |
| 9,101,534 B2 | 8/2015 | Bochenko |
| 9,199,042 B2 | 12/2015 | Farrar et al. |
| 9,272,099 B2 | 3/2016 | Limaye et al. |
| 9,336,669 B2 | 5/2016 | Bowden et al. |
| 9,402,967 B1 | 8/2016 | Vitello |
| 9,463,310 B1 | 10/2016 | Vitello |
| 2002/0023409 A1 | 2/2002 | Py |
| 2002/0133119 A1 | 9/2002 | Eakins et al. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2006/0084925 A1 | 4/2006 | Ramsahoye |
| 2007/0106234 A1 | 5/2007 | Klein |
| 2007/0142786 A1 | 6/2007 | Lampropoulos et al. |
| 2008/0068178 A1 * | 3/2008 | Meyer ................ B65D 41/3423 340/572.8 |
| 2009/0149815 A1 | 6/2009 | Kiel et al. |
| 2010/0084403 A1 | 4/2010 | Popish et al. |
| 2010/0126894 A1 | 5/2010 | Koukol et al. |
| 2011/0044850 A1 | 2/2011 | Solomon et al. |
| 2011/0046550 A1 | 2/2011 | Schiller et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2014/0155868 A1 | 6/2014 | Nelson et al. |
| 2015/0305982 A1 | 10/2015 | Bochenko |
| 2016/0144119 A1 | 5/2016 | Limaye et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |

\* cited by examiner

DETAIL B

DETAIL C

DETAIL D

DETAIL A

TAMPER EVIDENT SHIELD ASSEMBLY WITH TRACKING

CLAIM OF PRIORITY

The present Non-Provisional patent application claims priority pursuant to 35 U.S.C. Section 119(e) to a prior filed Provisional patent application, namely, that having Ser. No. 61/984,347 filed on Apr. 25, 2014, as well as to another prior filed Provisional application, namely, that having Ser. No. 61/913,571 filed on Dec. 9, 2013, the contents of which are both incorporated herein by reference in their entireties.

BACKGROUND OF THE INVENTION

Field of the Invention

This invention is directed to a tamper evident shield assembly for the port of a container such as, but not limited to, an intravenous (IV) bag or container, a medicine vial or another type of container that will typically be, but does not necessarily have to be, related to medicine. The inventive tamper evident shield assembly includes a housing that has a hollow interior as well as movably connected first and second housing segments that are selectively disposed from an open orientation and into a closed orientation. Additionally, a lock assembly is disposed on an exterior of the housing and operates to maintain the first and second housing segments in the closed orientation. The inventive tamper evident shield assembly also includes a frangible structure which, along with other structure, serves to assist with providing an indication as to if and when the inventive shield assembly has been tampered with.

Description of the Related Art

In medical care facilities across this country and in other countries, it is common practice for medical doctors and other authorized medical personnel to order that a patient be given a drug or medication orally, as well as by injection and by intravenous (IV) administration. As just one example of how common this is, it is currently estimated that more than 16 billion injections are administered on a worldwide basis in any given year.

Also, and as the costs of many new and other drugs can be quite expensive, it is becoming relatively common in hospital settings for a number of syringes and other types of medical containers to be pre-loaded or filled by a pharmacist, or other authorized personnel within a hospital or similar facility, at an appropriate location for subsequent dispensing to one or more patients. The pharmacy or other location where syringes and other types of medical containers are filled can and often will be located in a remote part of the hospital, relative to the patient care area where the medicine is to be administered. In some cases, the pre-loading of syringes and other medical containers occurs in another building or facility entirely, often referred to as "third party pharmacies." This may even be a growing trend among hospitals to limit certain costs. Regardless, pre-loaded syringes and other medical containers can be delivered to a large number of nurse's stations in multiple hospital or medical buildings. Because many nurse's stations are typically remotely located from the pharmacy or other station that pre-loads syringes and the like with drugs, these are quite often given to another person for delivery to a nurse's station, for subsequent dosing of the patient by qualified personnel. From the foregoing, it may be understood that during the course of loading a syringe or other medical container with a drug, and delivering it to a nurse's station or to a patient, numerous personnel can easily be involved with the handling of the device and the drug inside.

Moreover, and especially in the case of a very expensive drug or an addictive drug that has been prescribed for a patient, such as morphine, there is some danger that a pre-loaded syringe or other medical container will be tampered with at some point by a person seeking to improperly gain access to the drug. This possibility can present real danger when an unauthorized person gains access to the contents of a pre-loaded syringe or other medical container. By way of examples only, the sterility of the syringe or medical container and/or its contents can become contaminated, or another possible outcome could involve the inappropriate substitution of some other, unauthorized substance in the syringe or other medical container, such as if saline solution were substituted for a dose of morphine. Thus, there is a problem of determining if a sealed, preloaded syringe or medication container has, or has not, been tampered with or has otherwise been exposed to contamination. These and related types of problems have been described in one or more of the present inventor's own previously granted U.S. patents, such as U.S. Pat. Nos. 8,348,895 and 8,591,462, both of which are incorporated herein by reference, as well as in other parties' patents, such as U.S. Pat. No. 5,328,474 to Raines.

However, certain problems remain in this particular field of art, despite the introduction of inventive products previously, such as those represented in the present inventor's own U.S. patents. For example, one problem relates to the ability to manufacture tamper evident devices in a manner that is both relatively easy and inexpensive, while another problem relates to the manner in which such tamper evident devices are assembled and placed on a syringe that has been pre-loaded with a drug, or on another device carrying a substance used to treat patients, such as an intravenous (IV) bag or medicine vial. Yet additional problems relate to the maintenance of sterility of such pre-loaded syringes and other medical containers during filling and storage at the manufacturing facility and during transport to and throughout the various hospital and medical buildings where they will be used. Accordingly, the present invention seeks to address such problems associated with the handling of tamper evident devices, whether as end caps or other closures that are used with syringes or as yet other containers associated with the storage and/or administering of medicine, and to address such problems regardless of whether they arise at the stage of manufacture, assembly, the loading of a drug or medicine, or further downstream, such as during their transport, storage or administration of same.

Therefore, there is a need for an improved, tamper evident device which is capable of being used with standard or conventional pre-loaded syringes, whether for administration of a drug orally or by injection, and with other medication administering or storing containers, in a manner which overcomes the problems and disadvantages that remain in this field of art, such as those referred to above. If any such improved tamper evident device were developed, it would preferably have appropriate and advantageous structural and operative features, and might include, but not be limited to, having an integral or one piece construction which facilitates a suitable interconnection with or mounting on a preloaded syringe or other container for medicine.

In addition, if any such improved tamper evident device were developed, it would preferably be structured to provide a clear and unmistakable indication of tampering or an attempt to gain access to the contents of the pre-loaded syringe or other container of medicine. Further, the structuring of any such tamper evident device, if one were developed, should be such as to prevent the opening thereof in order to provide access without requiring the complete or partial destruction of the tamper evident device, so that as a result, such structural damage to the device would be clear evidence of an attempted tampering. Finally, if any such improved tamper evident device were developed, it should also be structurally and operatively reliable, while being capable of being quickly and easily mounted in a protective position relative to the port, closure or syringe cap, etc. associated with the medication storage or administering container, in order to facilitate widespread use and acceptance throughout the medical field.

SUMMARY OF THE INVENTION

The present invention is intended to present a solution to these and other needs which remain in the relevant field of art, and as such, is directed to a shield assembly for a port or closure associated with any one of a variety of different containers specifically including, but not limited to, medical containers such as a medication vial, an Intra-Venous (IV) bag or container, an oral syringe, an injection syringe, and the like.

More specifically, the shield assembly of the present invention includes a housing having a hollow interior and additionally, comprises a first housing segment and a second housing segment which are either hingedly or otherwise movably connected to one another. As such, the first and second housing segments are collectively and relatively disposable into either an open orientation or a closed orientation. Moreover, the boundaries and/or dimensional parameters of the housing's aforementioned hollow interior is effectively determined when the housing is disposed in the closed orientation. In addition, the first and second housing segments are cooperatively dimensioned and configured to include a cooperative overall structure that define a dimension of the hollow interior of the housing which is sufficient to enclose the port or closure of the medical or other appropriate container. As explained in greater detail hereinafter, the dimension and configuration of the hollow interior of the housing may at least partially correspond to that of the closure/port of the container, if not substantially correspond thereto, so that access to the closure/port is restricted. However, and as will also be described in greater detail herein, the inventive shield assembly will ideally also include a tamper evident structure to readily signal when an unauthorized person has attempted to access or might have gained access to the port or closure, and it follows, to the contents of the medical or other container.

Therefore, additional structural and operative features of the shield assembly of the present invention include a lock assembly connected to the housing, and in the illustrated embodiments, to each of the first and second housing segments. For example, and in at least one preferred embodiment, the lock assembly includes a male member and a female member, each connected to and movable with a different one of the first and second housing segments. Further, the male and female members are cooperatively dimensioned and configured to assume an interlocking engagement with one another, when in a locked position. Accordingly, the female member of the lock assembly includes an opening through which the male member passes as it is disposed into and out of a locked position and an unlocked position. Additionally, relatively close dimensional tolerances exist between the outer surface(s) of the male member and the interior periphery of the opening of the female member. As a result, when in the locked position, the male member effectively "fills" or closes the opening of the female member. This corresponding, relatively close dimensional tolerance will prevent or at least restrict the successful application of a tool or instrument by an unauthorized person to the lock assembly, in an attempt to access the port/closure and the contents of the container, without an indication of tampering.

Accordingly, another preferred feature of the shield assembly of the present invention is the provision of a tamper evident structure. In the more preferred embodiments, the tamper evident structure comprises a frangible structure connected to the housing, and more specifically, to the aforementioned lock assembly. As such, the structural and operative features of the frangible structure will provide a clear indication of tampering when access to the port/closure and contents of the associated container is attempted or accomplished. In more specific terms, the frangible structure preferably comprises at least one, but in some embodiments a plurality of frangible members. The one or more frangible members are disposed immediately adjacent and/or are formed to be contiguous to the inner periphery of the opening of the female lock member. Due to the close tolerances between the male and female lock members, as set forth above, passage of the male member through the opening of the female lock member will result in movable engagement or contact between the male member and the one or more frangible members surrounding and/or defining the periphery of the opening in the female lock member.

Additionally, the one or more frangible members are preferably flexibly attached to the female lock member in order to accommodate such relative movement and/or movable engagement between the male member and the frangible structure. As a result, the flexible structuring of the one or more frangible members facilitates the passage of the male member through the opening of the female member and into the locked position, upon being moved from the unlocked position, without structurally affecting or compromising the frangible members. Yet another preferred feature of the present invention includes a restrictor disposed on the female lock member immediately adjacent to and/or in movement restricting relation with the frangible structure. As such, passage of the male member through the opening of the female member, when moving from an unlocked position into a locked position, will limit the movement or flexure of the one or more frangible members as the frangible structure comes into movable contact or engagement with the male member. This restriction of the movement or the flexure of the one or more frangible members will prevent detachment thereof from the female lock member, as the male member passes through the opening from an unlocked position to a locked position.

In contrast, when the male member is moving from the locked position and into the unlocked position, the relative dimensions, configurations and overall structures of the male lock member and female lock member results in an abutting engagement of the male lock member with the one or more frangible members. As such, when a person attempts to remove the inventive shield assembly so as to access the port or closure of the medical container, this abutting engagement will result in an excessive flexure of the one or more frangible members, and a detachment thereof from both the female lock member and remainder of the frangible structure. In turn, an at least partial detachment of the frangible structure, including the detachment of one or more frangible members from the female lock member, will result in an enlargement of the opening of the female member. Such an enlargement will likely be sufficient to prevent the aforementioned interlocking engagement from being resumed between the male member and a female member in the locked position. Additionally, the close dimensional tolerances between the male and female lock members will likely be eliminated due to the location of the one or more frangible members about the periphery of the opening of the female lock member. Further, the enlargement of the opening associated with the female lock member will allow an unencumbered passage of the male member through the opening of the female member, when the one or more frangible members has or have been removed, and the opening has been correspondingly enlarged.

As an intended result, the inability of the male member and female member to assume the interlocking engagement and/or the locked position therebetween will provide clear evidence that the inventive shield assembly has been tampered with. Therefore, an attempted or accomplished access to the port/closure of the container, as well as the contents thereof, will prevent re-use of the same shield assembly, because the male and female lock members will not be able to interlockingly engage one another into the closed position.

It is recognized that one way of overcoming the observable evidence arising from a person having tampered with the shield assembly of the present invention would be for him or her to replace the original shield assembly with a second or new, and un-used shield assembly. Accordingly, one or more preferred embodiments of the shield assembly of the present invention further include a tracking assembly, which in at least one embodiment comprises an indicator segment including a "tracking structure." The tracking structure is disposed in an observable location that is preferably, but not necessarily, located on the exterior of the housing. Also, the tracking structure preferably comprises one or more predetermined codes capable of readily identifying and distinguishing each of the shield assemblies and/or housings associated therewith, from one another. The use of a predetermined code may include a variety of coded indicia such as, but not limited to, a bar code, which may also be electronically readable. Further, the predetermined code including coded indicia may be in the form of an optically scanned code, unique alpha/numerical serial number or other forms of coded indicia. Such coded indicia may be disposed on at least one portion of the housing or alternatively, on a plurality of the different components thereof. As indicated, the coded indicia is not necessarily limited to a bar code, but may assume other forms of code which may be electronically readable as well as visually observable. Further, the coded indicia applied to each of a plurality of the shield assemblies will ideally differ, so as to clearly distinguish one shield assembly from another. As a result, the coded indicia applied to the different housings or other portions of a plurality of shield assemblies will provide specific identifying information or data relating to a specific shield assembly.

Moreover, when considered to be appropriate and/or desirable, the coded indicia may be disposed on each of the plurality of components of a single shield assembly. When the coded indicia is disposed on different components of the same shield assembly, it may be identical or at least sufficiently similar so as to facilitate a determination that the various components are associated with the same shield assembly.

Additionally, the coded indicia should preferably serve to not only distinguish one shield assembly and/or housing from another but to determine the site and/or identity of the original manufacturer, as well as the distribution route from its manufacturing site to any holding site(s) and on to its eventual end point of intended use, which is most likely for the actual dispensing of medicine to a patient in accordance with an authorized prescription. The coded indicia in this instance should similarly include electronically or otherwise readable data to facilitate the determination of identifying shield assembly information such as, but not limited to, lot number, date of manufacture, serial numbers and/or component identifying information, if any, and the like. The procedure used to apply the coded indicia to the selected shield assembly as/or its components should be such as to not interfere with or derogatorily affect efficient manufacturing and/or assembly techniques and procedures for the shield assembly.

It can be appreciated that the provision of the inventive shield assembly with an indicator segment, such as a tracking assembly, will allow authorized personnel to determine whether one of these shield assemblies, once disposed in a closed orientation and in a locked position about a port/closure of a container, is, in fact, the original shield assembly that was applied, by checking the contents of the coded indicia. In practice, the tracking structure and any coded indicia would typically be recorded when a given shield assembly is applied in a closed orientation to a port/closure. This would prevent unauthorized personnel from attempting to substitute a second shield assembly for the original shield assembly, wherein the original shield assembly has been tampered with or removed to accomplish access to the port/closure and contents of the container associated therewith.

Yet another embodiment of the tracking assembly comprises a tracking structure which is preferably in the form of at least one RFID structure. While the description of this embodiment of the tracking assembly refers to a single RFID structure, it is emphasized that a plurality of such RFID structures could be utilized by being secured to different parts of the shield assembly, housing, lock assembly, etc.

As already described above, the first and second housing segments are movably connected to one another, and preferably, are hingedly connected to each other along a common, longitudinally disposed seam or junction. Accordingly, it is important to align the male locking member with the opening of the female locking member in order to accomplish the intended interlocking engagement between them. Therefore, one or more preferred embodiments of the shield assembly of the present invention include a stabilizing assembly. The stabilizing assembly includes an insert segment and a slot segment, with preferably, each disposed on and movable with a different one of the first and second housing segments. In operation, the insert segment is movable with a corresponding one of the first or second housing segments into an interior of the slot segment associated with the other of the first and second housing segments, as the first and second housing segments are disposed and moved relative to one another into the closed orientation.

Further, the thickness and/or transverse dimension of both the insert segment and the interior of the slot segment are such as to restrict movement of the insert segment when disposed within the interior of the slot segment. As a result, the first and second housing segments, respectively attached to the insert segment and the slot segment, will also be limited or restricted in their relative movement. In turn, the male lock member will be accurately or appropriately aligned within the opening of the female lock member, as the first and second housing segments are disposed into the closed orientation, concurrently with the insert segment passing into the interior of the slot segment. The aforementioned restricted relative movement of the insert segment and slot segment will be primarily, but not exclusively, in a direction corresponding to the longitudinal axis or the longitudinal seam, junction or hinge about which the first and second housing segments move relative to one another, as they are being disposed from an open orientation and into a closed orientation.

Yet another structural and operative feature may be incorporated in one or more embodiments of the shield assembly of the present invention, which involves the inclusion of a latch assembly. In the illustrated embodiment, the latch assembly includes an insert segment and a slot segment of the type described above with relation to the stabilizing assembly. Moreover, the latch assembly may be incorporated within and/or as part of the stabilizing assembly when both the stabilizing assembly and the latch assembly are structurally a part of the same shield assembly. Therefore, whether the latch assembly is used independently of or in combination with the stabilizing assembly, it comprises a plug mounted on and extending outwardly from a surface of an insert segment. The latch assembly further comprises a recess formed on the slot segment and disposed in at least partially aligned and receiving relation to the plug, when the first and second housing segments are disposed in the closed orientation. Therefore, when in the closed orientation, the plug will be at least partially inserted within the recess in a manner so as to establish a substantially fixed, interconnecting engagement therebetween. As a result, even if an unauthorized person attempts to defeat the aforementioned lock assembly, it will still not serve to open the housing and/or dispose the first and second housing segments in the open orientation. This is due to the fact that the latch assembly is located within the hollow interior of the housing when in its closed orientation. Therefore, the preferred plug and recess of the latch assembly described above will still be maintained in interlocking engagement with one another, which will also serve to maintain the first and second housing segments, and therefore the shield assembly itself, in the aforementioned closed orientation. If the unauthorized person attempts to use greater force to open the latch assembly, it will almost certainly result in at least partial destruction of the housing or portions thereof, and again, provide a clear indication that tampering has been attempted and/or access has been accomplished. It should additionally be appreciated that if such destruction of the original housing occurs, the aforementioned indicator segment and tracking structure, if utilized, will allow authorized personnel to easily and quickly determine that a second shield assembly has been substituted for the original shield assembly used to enclose and prevent access to the port/closure of a given container.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
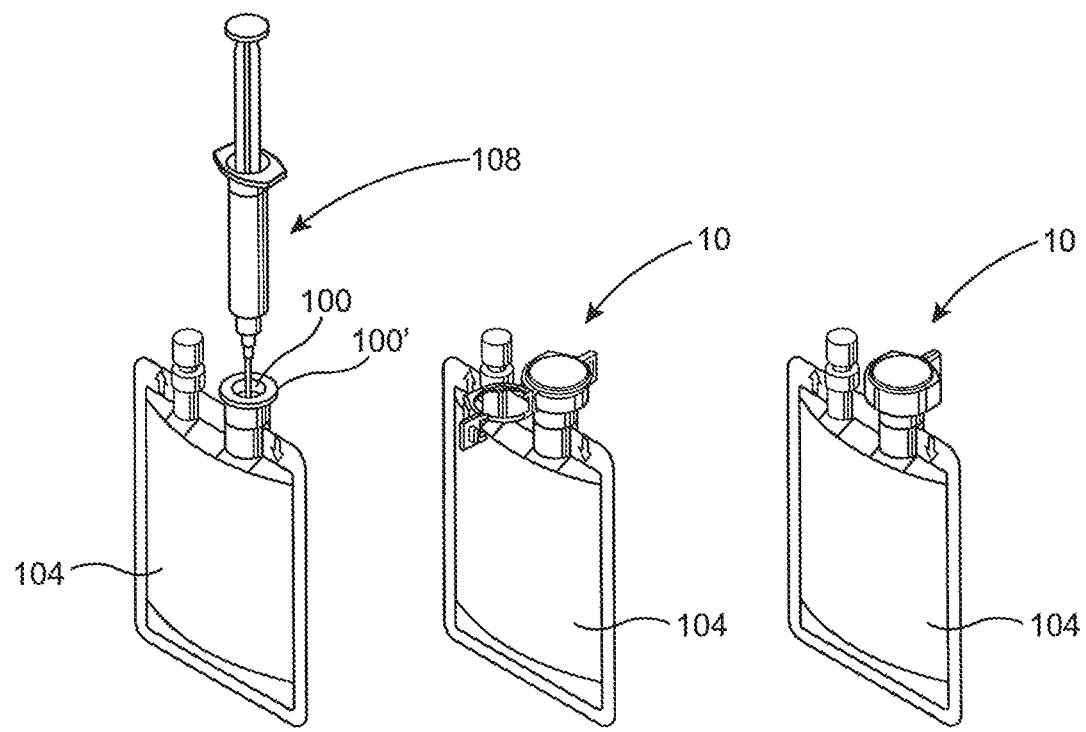
FIG. 1 is a collective, perspective view of an intravenous (IV) bag or container and with one embodiment of the inventive tamper evident shield assembly being applied to a port thereof.
Figure 2:
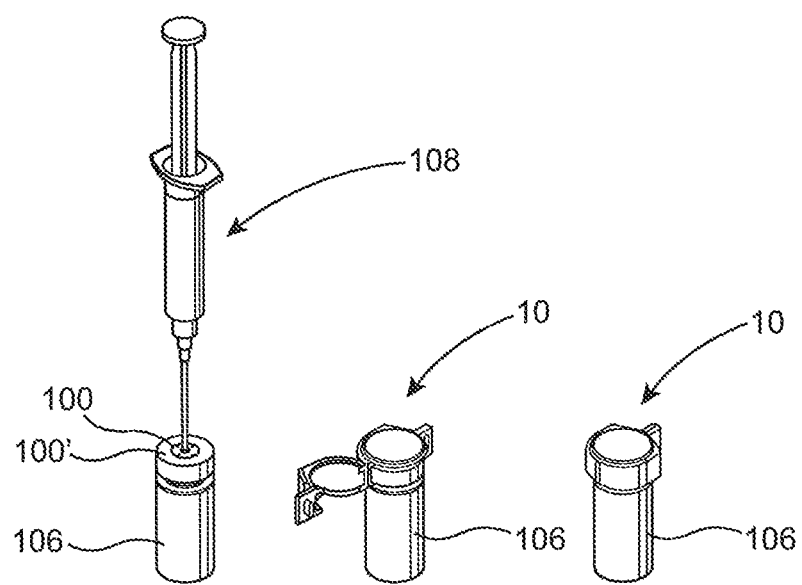
FIG. 2 is a collective, perspective view of a medicine vial or like container and with the inventive shield assembly shown in FIG. 1 being applied to a port thereof.

As represented in the accompanying Figures, the present invention is directed to a shield assembly, and is generally indicated as 10. As will be explained in greater detail hereinafter, the inventive shield assembly 10 is dimensioned, configured and structured to shield, protect and enclose a port or other closure as indicated at 100 or 100' in the drawings. The terms "port" and "closure" may be used interchangeably herein and in either case, the port or closure 100 or 100' will be of the type commonly associated with a variety of different containers, specifically including, but not limited to medical containers. As represented in FIGS. 1 and 2 and in some of the remaining Figures described herein, the medical containers may include an intravenous (IV) bag or like container, such as indicated in FIG. 1 at 104, a medicine vial such as indicated in FIG. 2 at 106, or the like and can include a syringe, such as an oral syringe. As also demonstrated in FIGS. 1 and 2, access to the interior of the IV bag 104 or medicine vial 106, whether authorized or not, is often accomplished through the use of a syringe as at 108.

Figure 3:
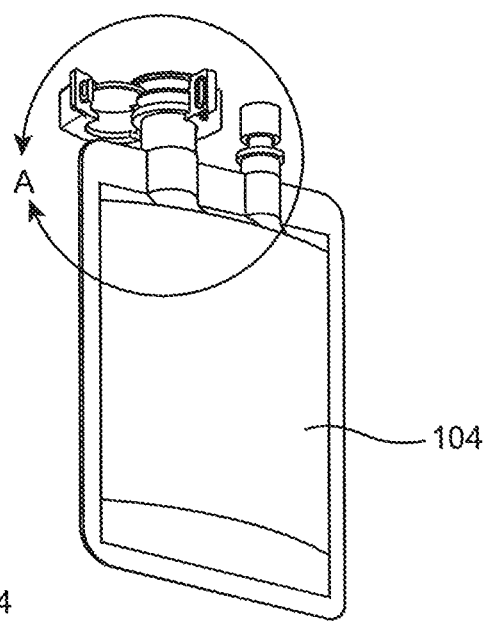
FIG. 3 is a perspective view of the inventive shield assembly shown in FIG. 1 illustrated in an open orientation as applied to the port of an IV bag or container.
Figure 4:
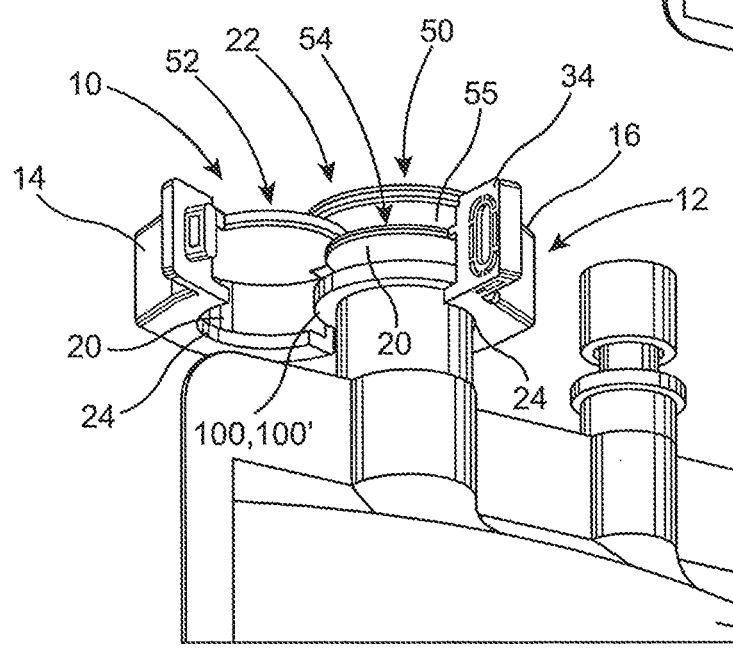
FIG. 4 is a detailed view in partial cutaway of the inventive shield assembly shown in FIG. 3.
Figure 5:
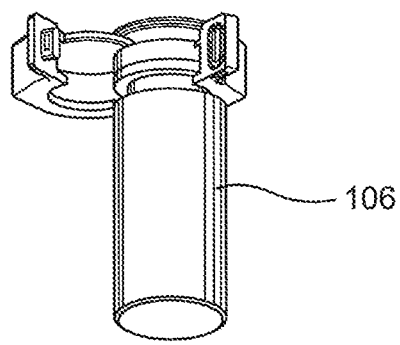
FIG. 5 is a perspective view of the inventive shield assembly of the embodiment shown in FIGS. 1-4 illustrating an open orientation as applied to the port of a medicine vial or like container.

Referring now more generally to FIGS. 1-3 and more specifically to FIGS. 4, 6 and 10-13, the inventive shield assembly 10 includes a housing, generally indicated at 12. The housing 12 includes a first housing segment and a second housing segment, 14 and 16, respectively. The housing segments 14 and 16 are movably connected to one another, which will preferably be by way of a hinged connection to one another along a common junction or seam 18, as is perhaps best illustrated in FIG. 9. The housing segments 14 and 16 are therefore capable of being selectively disposed between an open orientation, as represented in FIGS. 1-5, 7-8, 12 and 13, and a closed orientation, as represented in FIGS. 1-2, 6 and 9. Further, the housing 12 includes an at least partially hollow interior 20, which is best defined when the shield assembly is disposed in the closed orientation. With regard to FIGS. 11 and 13, it can be appreciated that the at least partially hollow interior 20 is dimensioned and configured relative to the port or closure 100, 100' so as to protectively enclose or enshroud the port or closure 100, 100'. It will further be appreciated that the hollow interior 20 may be defined by the interiors of one or both of the housing segments 14 and 16, with the boundaries of the hollow interior 20 best defined when the first and second housing segments 14 and 16 are in the closed orientation. In addition, the housing 12 includes a closed end which may be defined by a base 22, shown in FIGS. 4 and 6, and an open end 24, shown in FIGS. 4 and 13, which may be defined by open ends of one or both of the housing segments 14 and 16.

In order to connect the shield assembly 10 with or mount it onto a port or closure 100, 100', the housing segments 14 and 16 are first disposed in an open orientation, wherein the housing 12 can next be moved into a surrounding relation to the port/closure 100/100'. Further, the initial positioning of the shield assembly 10 is clearly demonstrated in FIGS. 4 and 13, wherein the open end 24 is disposed beneath and in surrounding relation to port/closure 100/100'. Concurrently, the closed-end or base 22 of the housing 12 is disposed above and in overlying relation to the port/closure 100/100' as is also shown in these Figures. When so positioned, the first and second housing segments 14 and 16 are then moved relative to one another into the closed orientation as represented in FIGS. 1, 2, 6 and 9.

Figure 6:
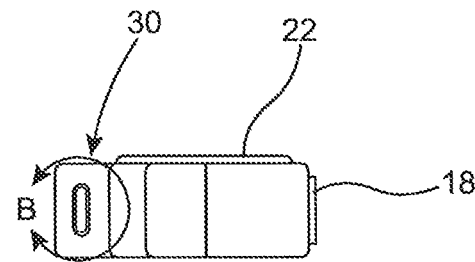
FIG. 6 is a side view of the inventive shield assembly of the present invention shown in a closed orientation.
Figure 7:
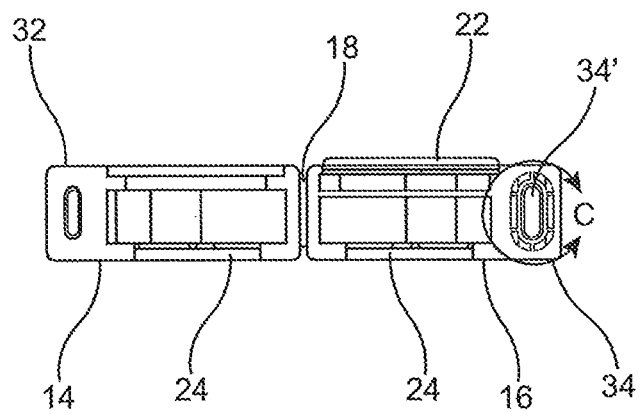
FIG. 7 is a side view of the embodiment of FIGS. 6 and 6A illustrating an open orientation and unlocked position.
Figure 8:
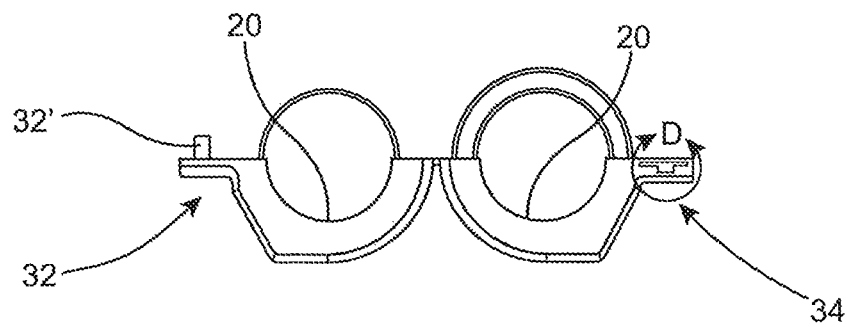
FIG. 8 is a bottom view of the embodiment of the inventive shield assembly as represented in FIGS. 1-7, in an open orientation.
Figure 10:
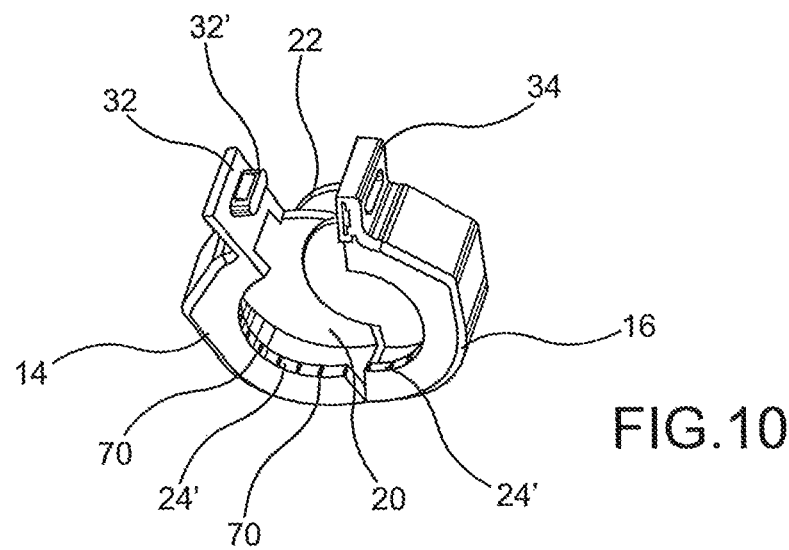
FIG. 10 is a perspective interior view of yet another preferred embodiment of the inventive shield assembly.
Figure 11:
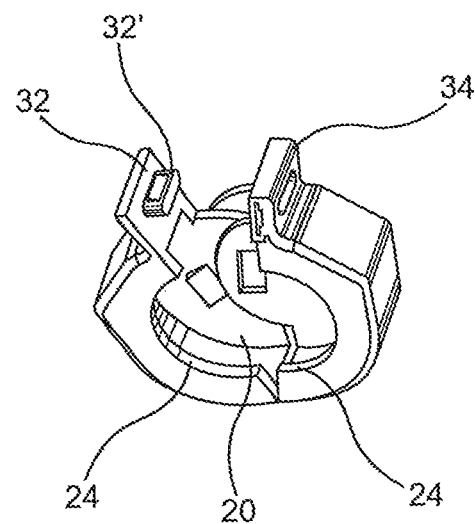
FIG. 11 is a perspective, partial interior view of yet another preferred embodiment of the shield assembly of the present invention.
Figure 12:
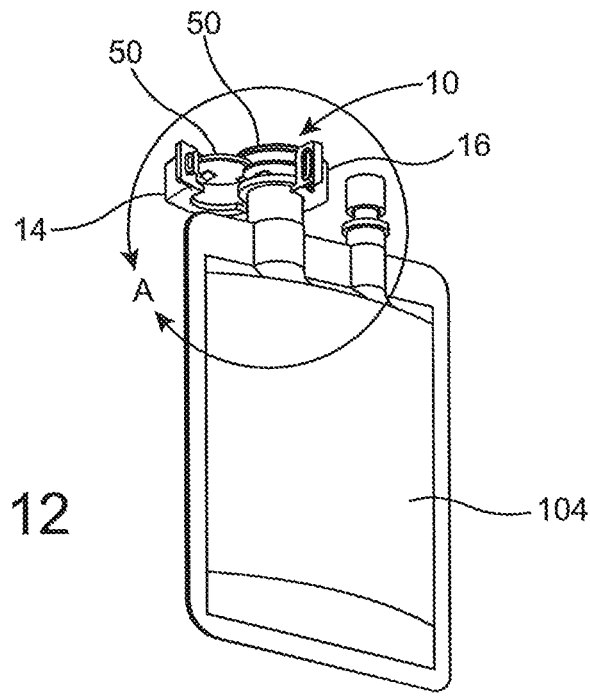
FIG. 12 is a perspective view of the embodiment of the shield assembly as represented in FIG. 11 and applied to the port of an IV bag or container.

With initial reference now to FIG. 6, an additional structural and operative feature of the shield assembly 10 includes the provision of a lock assembly, as is generally indicated at 30. As perhaps best shown in FIGS. 7-8 and 10-11, the lock assembly 30 includes a male lock member 32 and a female lock member 34. The male lock member 32 includes an outwardly protruding male segment 32' as shown in FIGS. 8 and 10, and the female lock member 34 includes an opening 34' as best illustrated in FIG. 7. Each of the male and female lock members 32 and 34 are connected to and movable with a different one of the first and second housing segments, 14 and 16. As will be explained in greater detail hereinafter, the lock assembly 30 is structured to maintain the first and second housing segments 14 and 16 in the closed orientation as the male segment 32' passes through the opening 34' of the female member 34, whereupon the male and female lock members, 32 and 34 respectively, will then be disposed in interlocking engagement with one another.

Figure 6A:
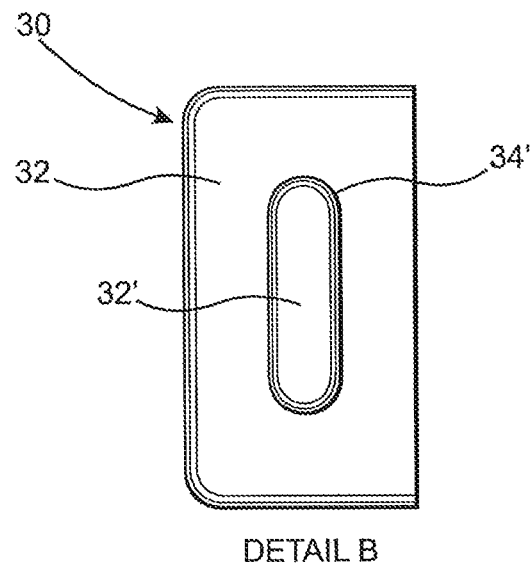
FIG. 6A is a detailed view of a lock assembly illustrating a closed orientation and locked position of the embodiment of FIG. 6.
Figure 7A:
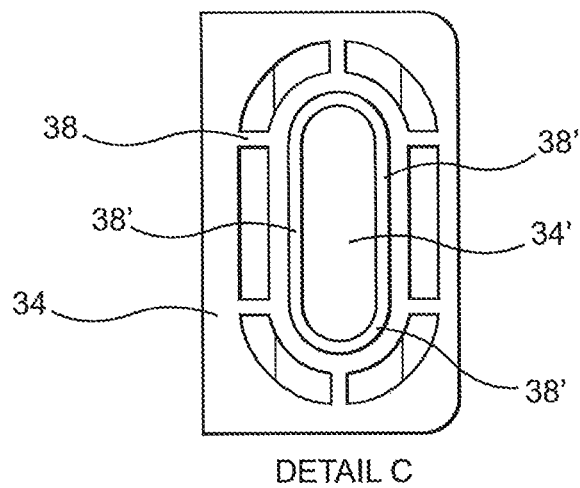
FIG. 7A is a detail view of a female member of the lock assembly of the embodiment shown in FIG. 7.
Figure 8A:
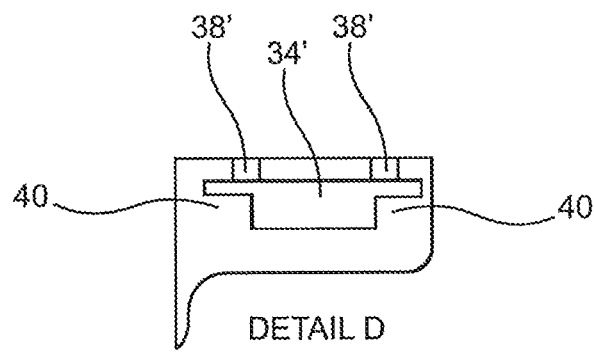
FIG. 8A is a detailed view of the female member of the lock assembly as represented in FIG. 8.

Furthermore, and in a most preferred embodiment of the inventive shield assembly 10, there will be a relatively close dimensional tolerance between the outer surface of the male segment member 32' and the interior periphery of the opening 34' of the female lock member 34. As a result, when in the locked position, the male segment 32' effectively "fills" or closes the opening 34' of the female member 34, as represented in FIG. 6A. This correspondingly close dimensional tolerance will restrict, if not altogether prevent, the successful application of a tool, tools or instruments to the lock assembly 30 in an attempt to open the shield assembly 10 and thereby, access the port/closure 100/100' and the contents of the container 104, 106, etc., without an indication of tampering.

More specifically, and with reference now to FIGS. 7-A and 8-A, the inventive shield assembly 10 will also include a tamper evident structure, which in the illustrated embodiment is preferably in the form of a frangible structure 38 connected to the female lock structure 24, as part of the aforementioned lock assembly 30. One purpose of the frangible structure 38 is to provide a clear indication of tampering when access to the port/closure 100/100' and contents of the associated container such as IV bag 104, or medical vial 106, etc. is either attempted or accomplished. In more specific terms, the frangible structure 38 comprises at least one, but in some embodiments, a plurality of frangible members 38' as shown in FIGS. 7-A, 8-A and 9. The frangible structure 38 is preferably disposed immediately adjacent and/or at least partially defines part of the inner periphery of the opening 34' of the female lock member 34. Due to the close tolerances between the exterior dimensions of the male segment 32' and the interior dimensions of the female lock member 34 including the inner periphery of the opening 34', as set forth above, passage of the male segment 32' through the opening 34' will result in movable engagement and/or contact between the male segment 32' and the frangible structure 38 surrounding and/or defining the periphery of the opening 34' in the female lock member 34.

With further reference to the tamper evident structure of the present invention and FIGS. 7-A, 8 and 8-A, it can be appreciated that the frangible structure 38 and the one or more frangible members 38' are, in at least one embodiment, flexibly attached to the female lock member 34. Such flexibility, or other appropriate structuring is provided and is sufficient to accommodate the relative movement and/or movable engagement between the male segment 32' and the frangible structure 38, as the male segment 32' passes through the opening 34' into the locked position. More specifically, the structuring of the one or more frangible members 38' facilitates the passage of the male segment member 32' through the opening 34' of the female member 34 into the locked position, without structurally affecting or detaching the frangible structure 38.

Additionally, and as illustrated in FIG. 8-A, another feature of the present invention includes a restrictor 40. The restrictor 40 is preferably disposed on the female lock member 34 immediately adjacent to and/or in movement restricting relation with the frangible structure 38 and/or 38'. As such, passage of the male segment 32' (best shown in FIG. 8) through the opening 34' of the female lock member 34 and frangible structure 38, when moving from an unlocked position into a locked position, will limit the movement or flexure of the one or more frangible members 38' and/or frangible structure 38, as the frangible structure 38 comes into movable contact or engagement with the male segment 32'. Such restriction of the movement or flexure will prevent or at least limit the possibility of detachment of the frangible structure 38 from the female lock member 34, as the male segment 32' passes through the opening 34' from an unlocked position and into a locked position.

Still referring to the tamper evident structure of the present invention and FIGS. 7-A, 8 and 8-A, it can be appreciated that the relative dimensions, configurations and overall structures of the male member 32 and female member 34 result in an abutting engagement of the male segment 32' with the frangible structure 38, when the male segment 32' is being moved in an opposite direction, from the locked position into the unlocked position. When sufficient pressure is applied to move the lock assembly 30 and the shield assembly 10 to an unlocked position, this abutting engagement will result in an excessive flexure of the one or more frangible members 38' and/or the frangible structure 38 and a complete or at least partial detachment of the frangible structure 38 from the female lock member 34. As a result, an at least partial detachment of the frangible structure 38, which may include the detachment of one or more frangible members 38' from the female lock member 34, will result in an enlargement of the opening 34' of the female lock member 34. Such an enlargement of the opening 34' will be sufficient to prevent the aforementioned interlocking engagement between the male member 32 and the female member 34 and will also failure to maintain the locked position of the lock assembly 30 and a closed position of housing segments 14 and 16 of the housing 12 of the shield assembly 10. Additionally, and due to the location of the one or more frangible members 38' and the frangible structure 38 relative to the opening 34', the close dimensional tolerances between the male segment 32' and the inner periphery of the frangible structure 38 and the overall dimension of the opening 34' will be eliminated. Accordingly, an application of pressure to the shield assembly 10 or lock assembly 30 which is sufficient to open the shield assembly 10 will cause a detachment of at least the frangible structure 38 and an enlargement of the opening 34' will allow for nearly unencumbered passage of the male segment 32' out of the opening 34' because the opening 34' has been correspondingly enlarged. As an intended result, the inability of the male member 32 and female member 34 to assume the interlocking engagement and/or the locked position, as represented in FIGS. 6 and 6A, will provide clear evidence of "tampering". Therefore, an attempted or accomplished access to the port/closure 100/100' of the container 104, 106, etc., as well as the contents thereof, will be readily observable and will likely prevent re-use of the original shield assembly 10, because the male and female lock members, 32 and 34 respectively, will not be able to engage and interlock with one another into a closed and locked position of FIGS. 6 and 6A.

Figure 9:
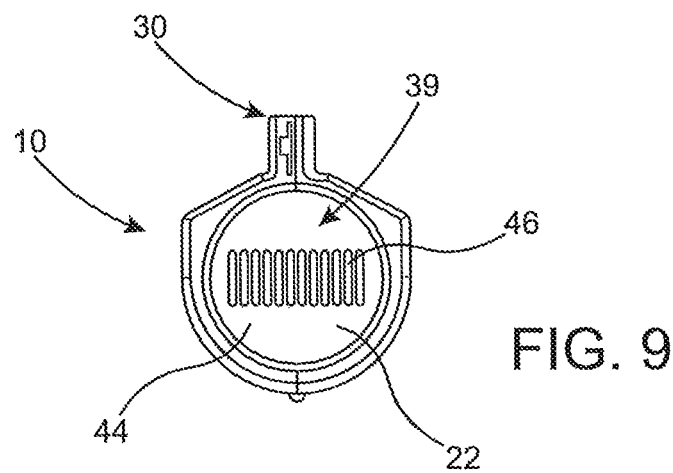
FIG. 9 is a top view of another preferred embodiment of the inventive shield assembly of the present invention including a tracking structure.

It is recognized that one way of overcoming the observable evidence indicating that a person has tampered with the shield assembly 10, would be for him or her to replace the original shield assembly 10 with a second or new, and un-used shield assembly. Accordingly, one or more preferred embodiments of the shield assembly 10 further comprise a tracking assembly generally indicated as 39 and including an indicator segment 44, as represented in FIG. 9. The indicator segment 44 preferably comprises a tracking structure 46 that is disposed in an observable location on the shield assembly 10. Preferably, but not necessarily, the tracking structure 46 is disposed on the exterior of the housing 12, such as on the exterior surface of the base 22. Additionally, the tracking structure 46 preferably comprises one or more predetermined codes structured to identify and distinguish each of the shield assemblies 10 and/or housing 12 associated therewith from one another. Any such predetermined code may further include coded indicia such as, but not limited to, a bar code, optical scan or other indicia that may also be electronically readable or electronically detectable with a suitable device. An acceptable or operable electronically detecting device or "reader" may include or communicate with suitable software, as a variety of such technologies is already known in the art, or alternatively, as may yet be developed. The predetermined code, coded indicia, etc. may also include unique alpha/numerical serial numbers and/or other forms of code. As noted above, such predetermined code may be disposed on at least a portion of the housing 12 or alternatively, on a plurality of the different components thereof.

Moreover, the predetermined codes or coded indicia, may have different data or content and may be applied to the housing 12 of each of a plurality of the shield assemblies 10. As such, each will differ from one another so as to clearly distinguish one shield assembly 10, and its components, from another, different shield assembly and its associated components. As a result, the predetermined codes applied to the different housings 12 or other portions of a plurality of different shield assemblies 10 will provide specific identifying information or data relating to a specific shield assembly. As a result, any one of a plurality of shield assemblies 10, housings 12 and associated components thereof may be distinguishable from one another. Further, each of the components of a common shield assembly 10, housing 12, etc. are capable of being identified as being associated with a common shield assembly, housing, etc.

Accordingly, when applicable, appropriate and/or desirable, a different predetermined code may be disposed on each of the plurality of components of each of a plurality of shield assemblies 10. Further, when the predetermined code is disposed on different components of the same shield assembly 10, it can be identical or at least sufficiently similar so as to facilitate a determination that the various components are associated with the same shield assembly 10. Additionally, the predetermined code in this instance should similarly include electronically, visually or otherwise readable data to facilitate the determination of relevant shield information such as, but not limited to, any or all of the following: lot number, date of manufacture, serial number, and other component identifying information. The procedure used to apply the predetermined code to the selected shield assembly 10 and/or its components should be such so as to not interfere with or derogatorily affect efficient manufacturing and/or assembly techniques and procedures associated with the inventive shield assembly 10.

Figure 14:
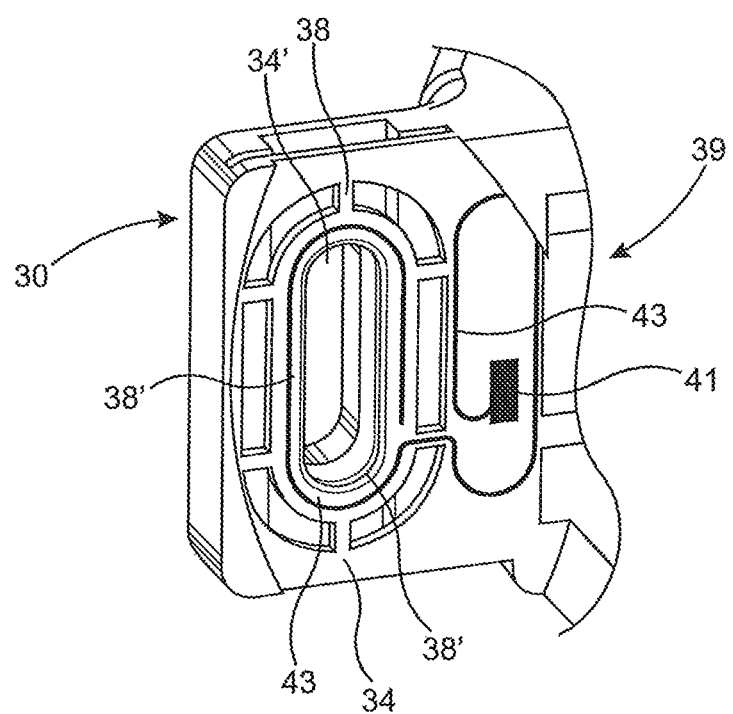
FIG. 14 is a perspective detailed view in partial cutaway of another preferred embodiment of the present invention relating to a tracking assembly.

With reference to FIG. 14, yet another embodiment of the tracking assembly is generally indicated as 39' and comprises a tracking structure which is preferably in the form of at least one RFID structure 41. While the description of this embodiment of the tracking assembly 39' is accomplished with reference to a single RFID structure 41, it is emphasized that a plurality of such RFID structures could be utilized by being secured to different parts of the shield assembly 10, housing 12, lock assembly 30 including, but not limited to, the male lock segment 32' and female lock member 34.

With further regard to the embodiment of FIG. 14, the at least one RFID structure 41 may be embedded by molding into the corresponding portion of the housing 12, such as into the female lock member 34. Similarly, the RFID structure 41 may include an antenna 43 similarly disposed on a corresponding portion of the housing 12 and or lock assembly 30. Therefore, the antenna 43 may be connected to one or more of the frangible members 38' as well as or independently of the frangible structure 38. In the assembled and operative mode, as represented in FIG. 14 an appropriate reader or electronic detecting device (not shown for purposes of clarity) will be operative to detect the presence of the at least one RFID structure 41 as well as the predetermined code which the RFID structure 41 has been programmed to generate or transmit. Therefore, in this embodiment the predetermined code, as set forth above, will again identify the specific shield assembly 10, housing 12 and/or components associated therewith.

As also set forth above, when the male segment 32' passes through the opening 34' into the locked position, the frangible structure 38 will remain intact and the housing segments 14 and 16 will remain in the closed position. However, upon forced removal of the male segment 32' from the locked position into the unlocked position, the frangible structure 38 will be at least partially detached causing a breaking and or separation of at least a portion of the antenna 43. As a result, the RFID structure 41 will not be operative and the detection of the RFID tag structure 41, by an electronic reader or detecting device will be prevented or significantly restricted. This will provide a clear indication that the two housing segments 14 and 16 had been previously opened, possibly indicating unauthorized tampering or attempted access to the port/closure 100/100'.

Also, if a different shield assembly and/or housing has been applied to the port/closure 100/100', the electronic reader or detection device will read a different predetermined code then that originally assigned to the RFID structure 41 of the original shield assembly 10 and/or housing 12 first applied to the closure/port 100/100', again providing a possible indication of tampering. It should therefore be apparent that in the additional preferred embodiment of FIG. 14, the tracking assembly 39, comprising the at least one RFID structure 41, includes its disposition and structuring to restrict the electronic detection thereof upon disposition of the lock assembly 30 into the unlocked position from the locked position. Further, the at least partial detachment of the frangible structure 38 from the lock assembly 30 and the female lock member 34 will serve to break or detach the antenna 43 relative to the remainder of the RFID structure 41, resulting in the prevention or significant restriction of electronic detection of the RFID structure 41 and/or the predetermined code associated therewith.

Therefore, the provision of the inventive shield assembly 10 with an indicator segment 44, such as a tracking structure 46, will allow authorized personnel to determine whether a given shield assembly 10 disposed in a closed orientation and in a locked position about a port/closure 100/100' of a container such as 104, 106, etc. is, in fact, the original shield assembly applied to a given port/closure 100/100' by checking the contents of the coded indicia. In practice, the tracking structure 46 and/or predetermined code associated there with will typically be recorded when a given shield assembly 10 is applied in a closed orientation to a port/closure 100/100'. This would prevent unauthorized personnel from attempting to substitute a second or different shield assembly for the original shield assembly, assuming that he or she tampered with the original shield assembly and removed it in order to accomplish access to the port/closure 100, 100' and contents of the container, such as 104, 106 associated therewith.

Figure 13:
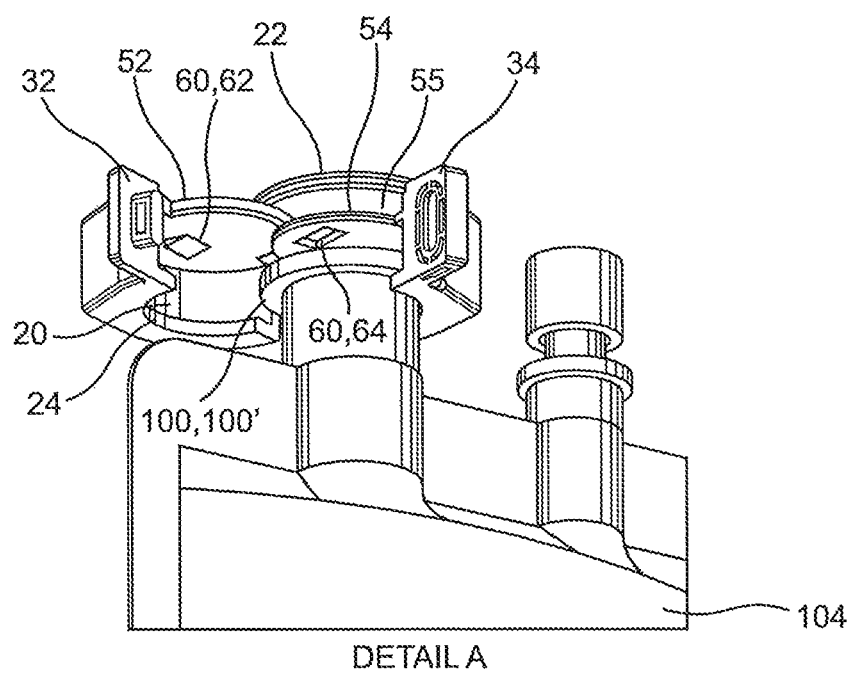
FIG. 13 is detailed, perspective view in partial cutaway of the embodiment of the inventive shield assembly as represented in FIGS. 11 and 12.

As set forth above, the first and second housing segments 14 and 16 are movably connected to one another, and in the preferred embodiments, are hingedly connected to one another along a common, longitudinally disposed seam or junction 18 as reflected in FIGS. 6-8. As has also been described previously herein, in order to accomplish an intended interlocking engagement of the male member 32 and female member 34 of the lock assembly 30, it is important to accomplish alignment of the male segment 32' with the opening 34' of the female member 34. Therefore, and with reference now to FIG. 12, one or more preferred embodiments of the shield assembly 10 of the present invention also include a stabilizing assembly generally indicated as 50. As illustrated in FIG. 13, the stabilizing assembly 50 includes an insert segment 52 and a slot segment 54, each disposed on and movable with a different one of the first and second housing segments, 14 and 16, respectively. In operation, the insert segment 52 is movable with a corresponding one of the first or second housing segments such as either 14 or 16, into an interior 55 of the slot segment 54 associated with the other of the first and second housing segments, as the first and second housing segments 14 and 16 are disposed and moved relative to one another into the closed orientation.

Further, the thickness and/or transverse dimension of both the insert segment 52 and the interior 55 of the slot segment 54 are such as to restrict movement of the insert segment 52 when disposed within the interior 55 of the slot segment 54. As a result, the first and second housing segments 14 and 16, to which either the insert segment 52 or the slot segment 54 are respectively attached, will also be limited or restricted in their relative movement. As a result, the male segment 32' associated with male lock member 32 will be accurately or appropriately aligned with the opening 34' of the female lock member 34, as the first and second housing segments 14 and 16 are disposed into the closed orientation, concurrently with the insert segment 52 passing into the interior 55 of the slot segment 54. The aforementioned, restricted relative movement of the insert segment 52 and slot segment 54 will be primarily, but not exclusively, in a direction corresponding to the longitudinal axis or the longitudinal seam, junction or hinge 18 about which the first and second housing segments 14 and 16 move, relative to one another, as they are being disposed from an open orientation into a closed orientation.

With reference again to FIG. 13, yet another structural and operative feature may be incorporated into one or more embodiments of the shield assembly 10 of the present invention and includes a latch assembly as is generally indicated at 60. The latch assembly 60 may include an insert segment 52 and a slot segment 54 of the type described above with relation to the stabilizing assembly 50. However, the latch assembly 60 may be incorporated within and/or as part of the stabilizing assembly 50, when both the stabilizing assembly 50 and the latch assembly 60 are structurally a part of the same shield assembly 10. Therefore, whether the latch assembly 60 is used independently of or in combination with the stabilizing assembly 50, it comprises a plug 62 mounted on and extending outwardly from a surface of the insert segment 52. The latch assembly 60 further comprises a recess 64 formed on the slot segment 54 and disposed in at least partially aligned and receiving relation to the plug 62, when the first and second housing segments 14 and 16 are disposed in the closed orientation. Therefore, when in the closed orientation, the plug 62 will be at least partially inserted within the recess 64 in a manner so as to establish a substantially fixed, interconnecting engagement therebetween.

As a result, the ability of an unauthorized person to attempt access and the unlocking of the aforementioned male lock member 32 and female lock member 34 associated with the lock assembly 30, will still not serve to open the inventive shield 10 and/or to dispose the first and second housing segments 14 and 16 into an open orientation. This is due to the fact that the latch assembly 60 is located within the hollow interior 20 of the housing 12 when in its closed orientation. Therefore, plug 62 and recess 64 of the latch assembly 60 will almost certainly still be maintained in substantially fixed, interlocking engagement with one another, which in turn, will serve to maintain the first and second housing segments 14 and 16 and the housing 12 in the aforementioned closed orientation. Should the unauthorized person persist and cause a forced opening of the latch assembly 60, this will almost certainly result in at least partial destruction of a portion of the housing 12, and again, this will provide a clear indication that tampering has been attempted and/or access has been accomplished.

If such destruction of the original housing occurs, authorized personnel can easily observe this and take appropriate action. Additionally, if the unauthorized person attempted to hide his or her tampering by applying a new or second shield assembly on the port or closure 100, 100' of the container, then the embodiment of the shield assembly 10 having an indicator segment 44 and tracking structure 46 would still allow authorized personnel to easily and quickly determine that a second shield assembly has been substituted for the original shield assembly used to enclose and prevent access to the port/closure 100/100' of a given container 104, 106, etc. as has been described previously herein.

With reference now to FIG. 10, yet another structural and operative feature of the shield assembly 10 of the present invention is represented. More specifically, an irregular surface configuration 70 such as a plurality of teeth, ribs, etc. can define and be formed in the peripheral region 24' of the housing, adjacent the open end 24, and ideally on each of the housing segments 14 and 16. This irregular surface configuration 70 facilitates a secure but removable gripping engagement with correspondingly disposed portions of the port/closure 100/100' when the housing segments 14 and 16 are moved into the closed orientation. The irregular surface configuration 70, which can include projecting teeth, facilitates the versatile use of the inventive shield assembly 10 on a variety of different port/closure 100/100' and serves to maintain the shield assembly 10 in closing, protective relation to the port/closure 100/100'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A shield assembly for a port of a container, said shield assembly comprising:
   a housing having a hollow interior and comprising a first housing segment and a second housing segment movably connected to one another,
   said first and second housing segments disposable in an open orientation and a closed orientation,
   said housing comprising an open end and an oppositely disposed closed end when said first and second housing segments are disposed in said closed orientation,
   said hollow interior being dimensioned and configured to enclose the port when in said closed orientation,
   a lock assembly comprising a male locking member and a female locking member disposed on said housing and operative to maintain said first and second segments in said closed orientation, when said lock assembly is in a locked position,
   said lock assembly including a frangible structure structured for at least partial detachment from said housing when said lock assembly is disposed into an unlocked position from said locked position,
   said locked position comprising said male and female locking members disposed in interlocking engagement with one another concurrent to said frangible structure mounted on said female locking member,
   said frangible structure flexibly disposed into said at least partial detachment from said female locking member upon disposition of said male locking member into said unlocked position, from said locked position, and
   said at least partial detachment defining a restrictive configuration of said lock assembly preventative of maintaining said lock assembly in said locked position.

2. The shield assembly as recited in claim 1 wherein said female locking member includes an opening dimensioned to receive said male locking member therein concurrently to said frangible structure flexibly connected to said female locking member in movably engaging relation to said male locking member.

3. The shield assembly as recited in claim 1 wherein said frangible structure comprises at least one frangible member disposed in removable, interconnecting relation between said frangible structure and said female locking member concurrent to passage of said male locking member through said opening into said locked position.

4. The shield assembly as recited in claim 3 wherein said at least one frangible member is disposed and structured for forced detachment from said interconnecting relation upon passage of said male locking member through said opening into said unlocked position.

5. The shield assembly as recited in claim 1 wherein said partial detachment comprises a predetermined enlargement of said opening; said predetermined enlargement sufficient to prevent retention of said male locking member in said interlocking engagement with said female locking member.

6. The shield assembly as recited in claim 1 wherein said lock assembly further comprises a restrictor disposed in movement restricting relation to said frangible structure, said restrictor disposed to limit flexure and said at least partial detachment of said frangible structure upon passage of said male locking member through said opening into said locked position.

7. The shield assembly as recited in claim 1 further comprising a tracking assembly disposed on said housing and structured to at least identify each of a plurality of housings from one another.

8. The shield assembly as recited in claim 7 wherein said tracking assembly comprises an indicator segment formed on said housing and including a tracking structure, said tracking structure disposed on said housing in an observable location.

9. The shield assembly as recited in claim 8 wherein said tracking structure includes a predetermined code structured to identify and distinguish each of a plurality of said housings from one another.

10. The shield assembly as recited in claim 7 wherein said tracking assembly comprises at least one RFID structure disposed on said housing and structured for electronic detection at least when said lock assembly is in said locked position.

11. The shield assembly as recited in claim 10 wherein said predetermined code is electronically readable.

12. The shield assembly as recited in claim 10 wherein said RFID structure is disposed and structured to restrict said electronic detection upon disposition of said lock assembly into said unlocked position from said locked position.

13. The shield assembly as recited in claim 1 further comprising a stabilizing assembly including an insert segment and a slot segment each disposed on and movable with a different one of said first and second housing segments; said stabilizing assembly structured to facilitate aligned disposition of said lock assembly into said locked position.

14. The shield assembly as recited in claim 13 wherein said insert segment is movable with a corresponding housing segment into movement restricting engagement within said slot segment, concurrent to movement of said first and second housing segments into said closed orientation.

15. The shield assembly as recited in claim 14 wherein said stabilizing assembly and said lock assembly are cooperatively disposed and structured to facilitate aligned, interlocking engagement of components of said lock assembly, concurrent to movement of said insert segment and said slot segment into said movement restricting engagement with one another.

16. The shield assembly as recited in claim 13 further comprising a latch assembly at least partially connected to and movable with each of said first and second housing segments into said hollow interior, when said housing is in said closed orientation.

17. A shield assembly for a port of a container, said shield assembly having a tamper evident structure and comprising:
a housing including a hollow interior and a first housing segment and a second housing segment movably connected to one another,
said first and second housing segments relatively movable to define an open orientation and a closed orientation of said housing;
said housing including oppositely disposed closed and open ends when said first and second segments are in said closed orientation,
said hollow interior and said open end cooperatively dimensioned and configured to concurrently receive and enclose the port when said housing is in said closed orientation,
a lock assembly formed on said housing and including a frangible structure; said lock assembly comprising a male locking member and a female locking member disposed in interlocking engagement with one another to define a locked position,
said female locking member including an opening dimensioned to receive said male locking member therein; said frangible structure flexibly connected to said female locking member in movably engaging relation to said male member,
said frangible structure flexibly disposed into at least partial detachment from said female locking member upon disposition of said male locking member into said unlocked position, from said locked position, and
said at least partial detachment defining a restrictive configuration of said lock assembly preventative of said interlocking engagement of said male locking and female locking members.

18. The shield assembly as recited in claim 17 further comprising a tracking assembly disposed on said housing and structured to identify and distinguish said housing from others of a plurality of said housings.

19. The shield assembly as recited in claim 18 wherein said tracking assembly comprises a tracking structure including a predetermined code structured to identify and distinguish each of a plurality of said housings from one another.

20. The shield assembly as recited in claim 19 wherein said predetermined code is electronically readable.

21. The shield assembly as recited in claim 18 wherein said tracking assembly comprises at least one RFID structure disposed on said housing and structured for electronic detection at least when said lock assembly is in said locked position.

22. The shield assembly as recited in claim 21 wherein said RFID structure is disposed and structured to restrict said electronic detection upon disposition of said lock assembly into said unlocked position from said locked position.

23. The shield assembly as recited in claim 22 wherein said RFID structure is disposed on said lock assembly and structured for detection and identification of said housing.

24. The shield assembly as recited in claim 23 wherein at least a portion of said RFID structure is disposed on said frangible structure and separable from said remainder of said RFID structure and structured to restrict said electronic detection upon said at least partial detachment of said frangible structure.

25. The shield assembly as recited in claim 24 wherein said RFID structure is disposed on said female locking member and comprises an antenna at least partially disposed on said frangible structure, said antenna separable from the remainder of said RFID structure upon said at least partial detachment of said frangible structure.

26. The shield assembly as recited in claim 17 wherein said partial detachment comprises an enlargement of said opening; said enlargement sufficient to prevent retention of said male locking member in said interlocking engagement with said female locking member.

27. A shield assembly for a port of a container, said shield assembly comprising:
a housing having a hollow interior and comprising a first housing segment and a second housing segment movably connected one another,
said first and second housing segments disposable in an open orientation and a closed orientation,
said housing comprising an open end and an oppositely disposed closed end when said first and second housing segments are disposed in said closed orientation,
said hollow interior being dimensioned and configured to enclose the port when in said closed orientation,
a lock assembly comprising a male locking member and a female locking member disposed on said housing and operative to maintain said first and second segments in said closed orientation, when said lock assembly is in a locked position,
said lock assembly including a frangible structure structured for at least partial detachment from said housing when said lock assembly is disposed into an unlocked position from said locked position,
said locked position comprising said male and female locking members disposed in interlocking engagement with one another concurrent to said frangible structure mounted on said female locking member,
said frangible structure further comprising at least one frangible member disposed in removable, interconnecting relation between said frangible structure and said female locking member concurrent to passage of said male locking member through said opening into said locked position, said at least one frangible member disposed and structured for forced detachment from said interconnecting relation upon passage of said male locking member through said opening into said unlocked position, and
said at least partial detachment defining a restrictive configuration of said lock assembly preventative of maintaining said lock assembly in said locked position.

\* \* \* \* \*